Figure 1:
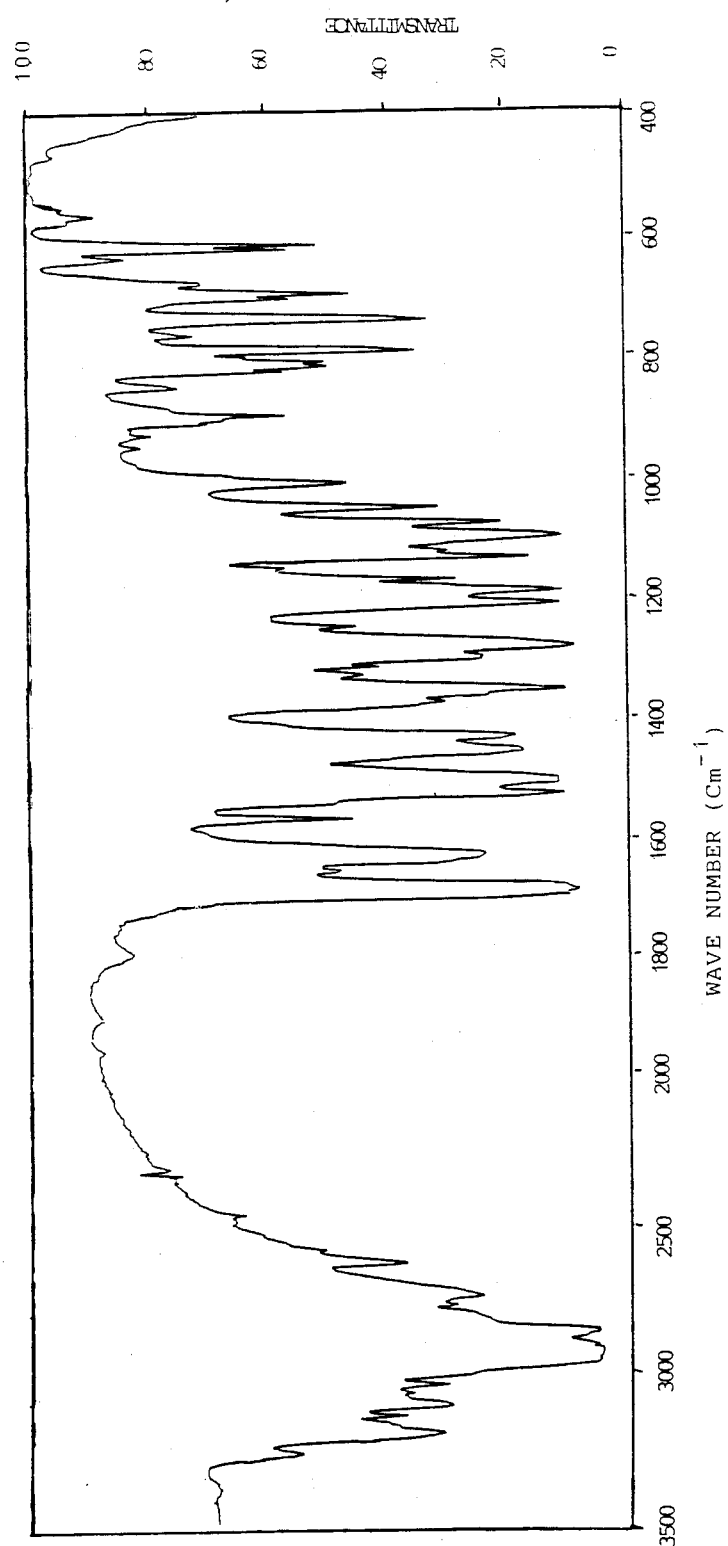

United States Patent [19]

Bradley et al.

[11] Patent Number: 4,983,617

[45] Date of Patent: Jan. 8, 1991

[54] STABLE CRYSTAL FORM OF 1,4-DIHYDRO-2-(IMIDAZOLYL-1-YLMETHYL)-6-METHYL-4-(3-NITROPHENYL)-PYRIDINE-3,5-DICARBOXYLIC ACID 3-ETHYL 5-METHYL DIESTER, HYDROCHLORIDE

[75] Inventors: Gerald Bradley, Weybridge; Geoffrey P. R. Carr, High Wycombe; Albert Opalko, Maidenhead; Richard J. Yarwood, Buckland, all of England

[73] Assignee: John Wyeth and Brothers Limited, Maidenhead, England

[21] Appl. No.: 283,352

[22] Filed: Dec. 12, 1988

[30] Foreign Application Priority Data

Dec. 17, 1987 [GB] United Kingdom ............... 8729471

[51] Int. Cl.$^5$ .................. C07D 403/06; A61K 31/44
[52] U.S. Cl. .................................. 514/341; 546/278
[58] Field of Search ........................ 546/278; 514/341

[56] References Cited

FOREIGN PATENT DOCUMENTS 2168969 7/1986 United Kingdom .

*Primary Examiner*—Mukund J. Shah
*Assistant Examiner*—P. Datlow
*Attorney, Agent, or Firm*—Arthur G. Seifert

[57] ABSTRACT

The invention concerns a new stable crystal form of anhydrous, crystalline 1,4-dihydro-2-(imidazol-1-ylmethyl)-6-methyl-4-(3-nitrophenyl)pyridine -3,5-dicarboxylic acid 3-ethyl 5-methyl diester hydrochloride, "having a melting point greater than about 215° C., an infra red spectrum (nujolmull) having sharp peaks at 3195 cm$^{-1}$, 3100 cm$^{-1}$, 2735 cm$^{-1}$ and 2625 cm$^{-1}$ and an x-ray powder diffraction pattern with specific peaks occurring at $2\theta = 12.3°$ and 44.5°."

2 Claims, 2 Drawing Sheets

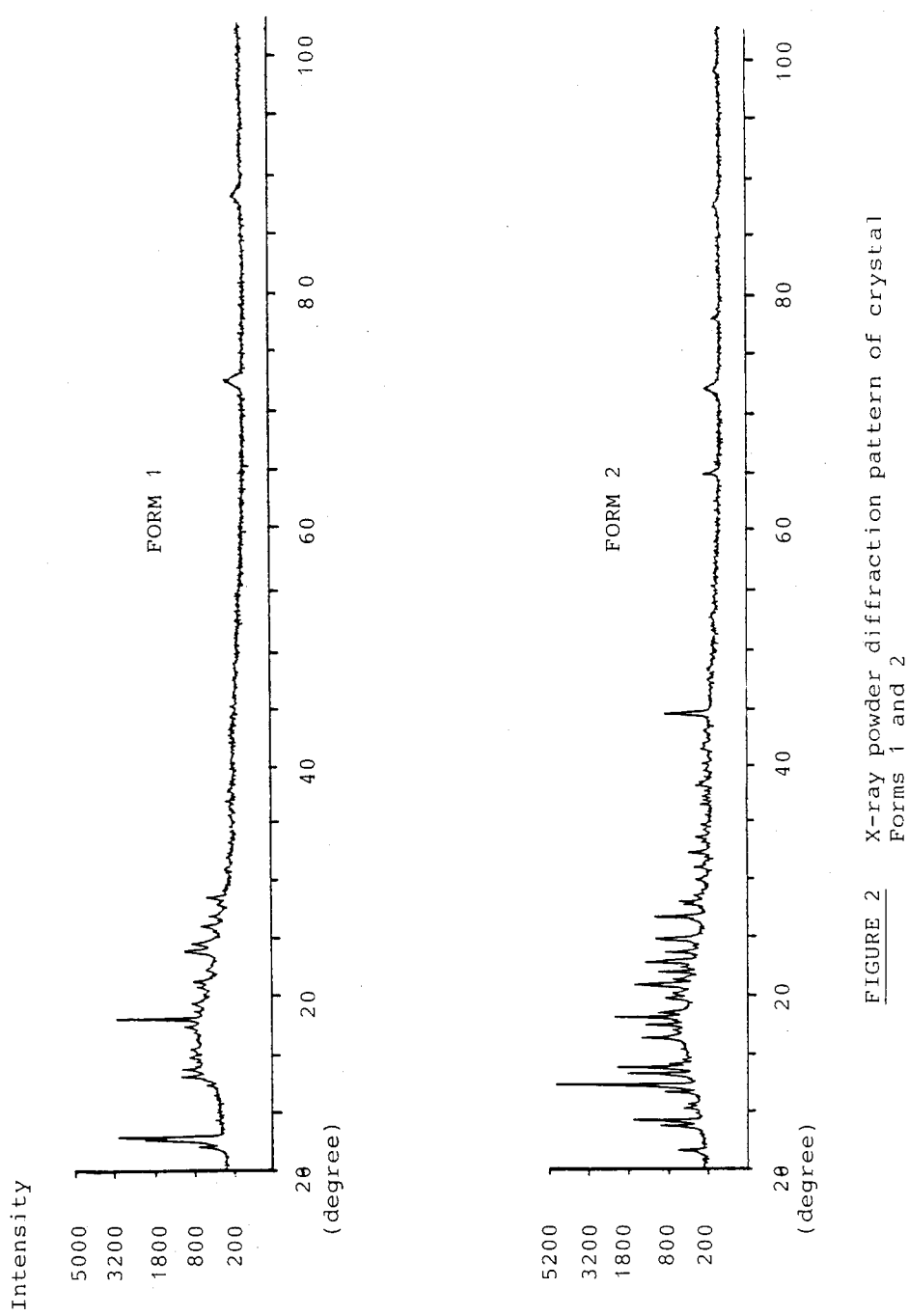
FIGURE 2    X-ray powder diffraction pattern of crystal Forms 1 and 2

STABLE CRYSTAL FORM OF 1,4-DIHYDRO-2-(IMIDAZOLYL-1-YLMETHYL)-6-METHYL-4-(3-NITROPHENYL)PYRIDINE-3,5-DICARBOXYLIC ACID 3-ETHYL 5-METHYL DIESTER, HYDROCHLORIDE

This invention relates to a crystal form, more particularly to a new crystal form of a 1,4-dihydropyridine compound, to a process for preparing it and to pharmaceutical compositions containing it.

Pharmaceutically active compounds are almost exclusively administered to humans in the form of formulations containing inert excipients and other ingredients. It is well recognised that for many drugs the formulation can have a dramatic influence on the overall effectiveness of the drug ranging from the expected to no effect at all. Accordingly, in the course of pharmaceutical research, once a new compound has been found from animal tests to possess valuable therapeutical properties, it is necessary to carry out a detailed investigation in order to devise a satisfactory formulation.

As a prelude to this a comprehensive study is made of the new compounds physical and chemical properties in what is known as a pre-formulation study aimed at determining a suitable form of the drug for providing a stable, effective and safe formulation.

In the course of the pre-formulation study adverse physical or chemical properties may be found which necessitate a change to another form of the compound. For example low aqueous solubility or instability problems may be encountered and in these cases the offending physico-chemical characteristics of the compound may be reduced or eliminated by conversion of the compound to a suitable salt form or by manipulation of the crystalline form, e.g. by micronization. Similarly, it is important to have a stable form of the new compound if at all possible otherwise problems can arise due to degradation resulting in shortened shelf-life and concomitant reduced and unpredictable efficiency. Those skilled in the art will be aware of other physical or chemical characteristics that lead to problems in the selection of a satisfactory form of a new compound.

In our UK Patent Publication No. 2168969A there are described a group of 1,4-dihydropyridines possessing antihypertensive activity and antithrombotic activity. One of the compounds mentioned in Publication No. 2168969A having the chemical name 1,4-dihydro-2-(imidazol-1-ylmethyl)-6-methyl-4-(3-nitrophenyl)pyridine-3,5-dicarboxylic acid 3-ethyl 5-methyl diester (A) has been chosen for further investigation as a potentially valuable drug on the basis of its combined potent antihypertensive and antithrombotic activity. The preparation of the hydrochloride salt of compound A is described in Example 1 of UK Patent Publication No. 2168969A. The process involved as a last step the recrystallisation of the product from ethanol/ethanolic HCl to give a hydrochloride hemihydrate salt having the melting point 144°-146° C. For the purposes of identification this form of the hydrochloride salt of compound A and the corresponding anhydrous salt will be referred to hereinafter as crystal Form 1.

During the preformulation investigation of the crystal Form 1 of the compound A, it was observed that the form possessed several very undesirable characteristics. Notably at high temperatures the form deteriorated, both physically and chemically, and under high humidity conditions the form was hygroscopic. In addition, the crystal Form 1 was corrosive to mild steel which meant that problems would arise with mechanical tooling should production be attempted.

Surprisingly we have found a different crystal form of the hydrochloride of formula A which possesses superior physico-chemical properties to the previously known Form 1. The new Form can be identified by its much higher melting point.

Accordingly in one aspect this invention provides a new crystal form of anhydrous 1,4-dihydro-2-(imidazol-1-ylmethyl)-6-methyl-4-(3-nitrophenyl)pyridine-3,5-dicarboxylic acid 3-ethyl 5-methyl diester, hydrochloride which form has a melting point greater than about 215°, and typically about 220°-245° C. For the purposes of identification the new crystal form will be referred to hereinafter as Form 2. When determining the melting point of the new crystal Form 2 it has been found that there is some variation in the observed melting point due to partial decomposition during heating at over 200°.

Nevertheless the melting point for Form 2 has been found to be substantially higher than that found for the previously known Form 1 (mp 144°-145° C. vide supra).

In addition, the new crystal Form 2 possesses an infrared spectrum and an X-ray powder diffraction pattern which are different from those of Form 1. FIG. 1 of the accompanying drawing shows the infra-red spectrum (nujol mull) of Form 2. Several sharp peaks in the spectrum are noteworthy because they are not seen in the infra-red spectrum of Form 1. These sharp peaks occur at 3195 cm$^{-1}$, 3100 cm$^{-1}$, 2735 cm$^{-1}$, and 2625 cm$^{-1}$. FIG. 2 of the accompanying drawings shows the X-ray powder diffraction pattern for both Form 1 and Form 2. Form 2 exhibits substantial differences in diffraction pattern over Form 1. In particular Form 2 has specific diffraction peaks occurring at $2\theta=12.3°$ and 44.5° and elsewhere. Accordingly, the new crystal Form 2 is readily distinguished from Form 1 by the higher melting point, the characteristic infra-red spectrum, and the X-ray powder diffraction pattern.

This invention also provides processes for preparing the new crystal Form 2. It has been found that crystal Form 2 can be prepared by refluxing the crystal Form 1 of 1,4-dihydro-2-(imidazol-1-ylmethyl)-6-methyl-4-(3-nitrophenyl)pyridine-3,5-dicarboxylic acid 3-ethyl 5-methyl diester, hydrochloride in isopropanol solvent and cooling. On cooling crystal Form 2 separates and can be collected by filtration.

Crystal Form 1 itself can be prepared as described in Example 1 of GB Patent Publication No. 2168969A where the product is obtained by treatment of the base with ethanol/ethanolic HCl. We have also found that crystal Form 1 may be prepared by treating the base with methanol/methanolic HCl.

In an alternative process crystal Form 2 may be prepared by treating 1,4-dihydro-2-(imidazol-1-ylmethyl)-6-methyl-4-(3-nitrophenyl)pyridine-3,5-dicarboxylic acid 3-ethyl 5-methyl diester as the free base in isopropyl alcohol with hydrochloric acid at an elevated temperature near to (e.g. within 10° C.) or at the reflux temperature of the mixture following by crystallisation on cooling.

The stability of the new crystal Form provided by this invention was measured relative to the known Form 1 in a series of experiments. These stability experiments are described below:

EXPERIMENT 1

Samples of crystal Form 1 and crystal Form 2 were stored in clear glass vials at 25° C. (closed containers), 37° C. (closed containers) and 37° C. (open containers, relative humidity=75%). Aliquots were sent for infrared spectroscopic investigation after 0, 2 and 6 weeks storage under the above conditions to see if there was any change in the crystal Form. The results are shown in the following table:

TABLE 1

| | Crystal Form 1 | | | Crystal Form 2 | | |
|---|---|---|---|---|---|---|
| | Storage Conditions | | | | | |
| Storage Period | 25° C. (closed) | 37° C. (closed) | 37° C. 75% RH (open) | 25° C. (closed) | 37° C. (closed) | 37° C. 75% RH (open) |
| 2 weeks | Still Form 1 with minor spectral changes | Still Form 1 with minor spectral changes | Completely converted to the hydrated form | Unchanged | Unchanged | Unchanged |
| 6 weeks | No further change from 2 weeks stage | No further change from 2 weeks stage | No further change from 2 weeks stage | Unchanged | Unchanged | Unchanged |

EXPERIMENT 2

Samples of crystal Form 1 and crystal Form 2 were stored in clear glass vials at 50° C. (closed containers) and 105° C. (open containers). Aliquots were removed for investigation by thin layer chromatography (TLC) after 0, 3 and 6 weeks storage under the above conditions.

The TLC system used silica gel 60 $F_{254}$ plates which were activated by heating at 105° C. before use. Two solvent systems were employed:

System 1—Toluene: absolute alcohol:0.880 ammonia=79:20:1 by volume

System 2—Dichloromethane:methanol:0.880 ammonia=89:10:1 by volume.

The developed plates, after drying, were visualised under UV light at 254 nm.

The amount of each sample loaded onto the plate was equivalent to 100 μg of free base from solutions in methanol.

Impurity levels were estimated by comparison with three samples run simultaneously containing the equivalent of 2 μg, 1 μg and 0.5 μg free base (corresponding to 2%, 1% and 0.5% levels respectively).

The results are given in the following Tables 2A and 2B.

TABLE 2A

| | TLC SYSTEM 1 | | | |
|---|---|---|---|---|
| | CRYSTAL FORM 1 | | CRYSTAL FORM 2 | |
| | Storage Conditions | | | |
| Storage Period | 50° C. (closed) | 105° C. (open) | 50° C. (closed) | 105° C. (open) |
| 0 Weeks | Main spot Rf 0.33 + 4 impurities — total < 2½% | | Main spot Rf 0.36 + 4 impurities — total < 2½% | |
| 3 Weeks | Main spot Rf 0.35 + 4 impurities — total < 2½% | Main spot Rf 0.35 + 5 impurities — total < 6% | Main spot Rf 0.39 + 4 impurities — total < 3% | Main spot Rf 0.39 4 impurities — total < 3½% |
| 6 Weeks | Main spot Rf 0.35 + 4 impurities — total > 3½% | Main spot Rf 0.35 + 5 impurities — total < 7% | Main spot Rf 0.33 + 4 impurities — total < 3% | Main spot Rf 0.36 + 4 impurities — total < 3½% |

TABLE 2B

| | TLC SYSTEM 2 | | | |
|---|---|---|---|---|
| | CRYSTAL FORM 1 | | CRYSTAL FORM 2 | |
| | Storage Conditions | | | |
| Storage Period | 50° C. (closed) | 105° C. (open) | 50° C. (closed) | 105° (open) |
| 0 Weeks | Main spot Rf 0.50 + 5 impurities — total < 3½% | | Main spot Rf 0.05 + 4 impurities — total < 2½% | |
| 3 Weeks | Main spot Rf 0.47 + 5 impurities total < 4½% | Main spot Rf 0.47 + 9 impurities total < 10% | Main spot Rf 0.43 + 4 impurities total < 3% | Main spot Rf 0.45 + 4 impurities total < 2½% |
| 6 Weeks | Main spot Rf 0.32 5 impurities — total < 5% | Main spot Rf 0.32 + 7 impurities — total < 11% | Main spot Rf 0.43 + 4 impurities — total < 3% | Main spot Rf 0.44 + 5 impurities — total < 4½% |

The results of Experiments 1 and 2 given in Tables 1, 2A and 2B above indicate that Form 2 is more stable both physically and chemically than Form 1, particularly at high temperatures and humid conditions.

The corrosive properties of the new crystal Form 2 were assessed relative to those of the known crystal Form 1 by carrying out the following test procedure:

Each crystal form was sprinkled as a powder onto (A) a 20 mm×70 mm strip of mild steel and (B) a 10 $mm^2$ patch of heavy duty tablet tooling steel, and then stored at 37° C. and relative humidity 75% of 24 hours. The extent of corrosion was assessed subjectively.

The following results were obtained:

|  | Mild Steel (A) | Heavy Steel (B) |
| --- | --- | --- |
| Crystal Form 1 | extensive corrosion | slight spots of corrosion |
| Crystal Form 2 | slight corrosion | no corrosion |

Crystal Form 2 was clearly superior to crystal Form 1 being much less corrosive to steel.

The hygroscopicity of the new crystal Form 2 was compared with that of known crystal Form 1 using the following general procedure:

Into the bottom of a plastic desiccator is placed 50 ml of a saturated salt solution for producing the desired constant relative humidity within the desiccator for the temperature under study (37°). A plastic insert with holes around the outside is placed over the saturated solution and a 12 cm petri dish is placed on the plastic insert leaving the holes partly uncovered.

A 40 mg sample in powder form of crystal Form 1 or crystal Form 2 is weighed into a glass vial and then placed on the petri dish. The desiccator is evacuated to seal it and stored at 37° C. for 7 days. After this time the vial is weighed to determine the equilibrium moisture content (EMC). Relative humidities used are 23%, 41%, 62%, 81% and 91%. EMC is calculated according to the formulae (1) and (2) below:

$$P = \frac{\left[W \times \frac{A}{100}\right] \pm B \times 100}{W - \left[W + \frac{A}{100}\right]} \quad (1)$$

where
P = % moisture dry basis
W = % initial sample weight in grams
A = % moisture at start
B = weight change at equilibrium in grams.

$$EMC = \frac{P}{100 + P} \times 100 \quad (2)$$

The initial moisture content is determined from the weight loss on heating 1 gm of material in a glass bottle at 105° C. for 2 hours.

The results found are given in the following table:

| | EMC values at 37° C. | |
| --- | --- | --- |
| Relative Humidity | Crystal Form 1 | Crystal Form 2 |
| 23% | 2.7% | 0 |
| 41% | 3.5% | 0 |
| 62% | 5.5% | 0 |
| 81% | 7.7% | 0 |
| 91% | 6.5% | 0 |

The results indicate that crystal Form 2 is much less hygroscopic than crystal Form 1.

In summary therefore the physical properties of the new crystal Form 2 are superior to those of the known Form 1 as regards stability, hygroscopicity and corrosiveness. Collectively said properties make crystal Form 2 eminently more suitable for use in formulations than crystal Form 1.

This invention also provides a pharmaceutical composition comprising anhydrous 1,4-dihydro-2-(imidazol-1-ylmethyl)-6-methyl-4-(3-nitrophenyl)pyridine-3,5-dicarboxyl acid 3-ethyl 5-methyl diester hydrochloride having a melting point greater than about 215° C.

The following Examples illustrate the preparation of the new crystal Form 2.

EXAMPLE 1

1,4-Dihydro-2-(imidazol-1-ylmethyl)-6-methyl-4-(3-nitrophenyl)pyridine-3,5-dicarboxylic acid, 3-ethyl 5-methyl diester, hydrochloride, crystal Form 2.

1,4-Dihydro-2-(imidazol-1-ylmethyl)-6-methyl-4-(3-nitrophenyl)pyridine-3,5-dicarboxylic acid 3-ethyl 5-methyl diester free base (100 grams) was added to a 1 liter sovirel reactor together with 400 mls of isopropyl alcohol. The mixture was stirred and heated to reflux. Further isopropylalcohol was added until a clear solution was obtained giving a total volume of about 600 mls. 30 mls of conc hydrochloric acid was added and the solution was cooled to 20° C. A solid crystallised and, after stirring at 20° C. for 30 minutes, was collected by filtration, washed with isopropyl alcohol (2 × 50 mls) and dried at 60° C. giving the title compound, m.p. 240° C.

| Analysis |
| --- |
| $C_{21}H_{22}N_4O_6 \cdot HCl$ requires C, 54.5; H, 5.0; N 12.1. |
| Found C, 54.8; H, 4.9; N 11.85. |

The infra-red spectrum of the product is shown in the accompanying FIG. 1. Characteristic sharp peaks appear at 3195 cm$^{-1}$, 3100 cm$^{-1}$, 2735 cm$^{-1}$ and 2625 cm$^{-1}$.

The X-ray powder diffraction pattern is shown in the accompanying FIG. 2 (lower spectrum).

We claim:

1. Anhydrous, crystalline 1,4-dihydro-2-(imidazol-1-ylmethyl)-6-methyl-4-(3-nitrophenyl)pyridine-3,5-dicarboxylic acid 3-ethyl 5-methyl diester hydrochloride in substantially pure form having a melting point greater than about 215° C., an infra red spectrum (nujolmull) having sharp peaks at 3195 cm$^{-1}$, 3100 cm$^{-1}$, 2735 cm$^{-1}$ and 2625 cm$^{-1}$ and an X ray powder diffraction pattern with specific peaks occuring at $2\theta = 12.3°$ and 44.5°.

2. A solid pharmaceutical composition comprising anhydrous, crystalline 1,4-dihydro-2-(imidazol-1-ylmethyl)-6-methyl-4-(3-nitrophenyl)pyridine-3,5-dicarboxylic acid 3-ethyl 5-methyl diester hydrochloride in substantially pure form having a melting point greater than about 215° C., an infra red spectrum (nujolmull) having sharp peaks at 3195 cm$^{-1}$, 3100 cm$^{-1}$, 2735 cm$^{-1}$ and 2625 cm$^{-1}$ and an X ray powder diffraction pattern with specific peaks occuring at $2\theta = 12.3°$ and 44.5° and a pharmaceutically acceptable carrier.

* * * * *